US012714461B2

(12) United States Patent
Arregui Altuna et al.

(10) Patent No.: US 12,714,461 B2
(45) Date of Patent: Aug. 25, 2026

(54) SURGICAL ACCESS PORT

(71) Applicant: DENEB MEDICAL, S.L., Donostia—San Sebastián (ES)

(72) Inventors: Juan Arregui Altuna, Donostia—San Sebastián (ES); Esteban Calvo Bernad, Saragossa (ES); Iker Mariñelarena Arrizabalaga, Donostia—San Sebastián (ES); Aritz Lazkoz Del Campo, Donostia—San Sebastián (ES)

(73) Assignee: DENEB MEDICAL, S.L., Donostia-San Sebastián (ES)

( * ) Notice: Subject to any disclaimer, the term of this patent is extended or adjusted under 35 U.S.C. 154(b) by 239 days.

(21) Appl. No.: 18/559,066

(22) PCT Filed: May 7, 2021

(86) PCT No.: PCT/ES2021/070317

§ 371 (c)(1),
(2) Date: Nov. 6, 2023

(87) PCT Pub. No.: WO2022/234159

PCT Pub. Date: Nov. 10, 2022

(65) Prior Publication Data

US 2024/0238007 A1 Jul. 18, 2024

(51) Int. Cl.
*A61B 17/34* (2006.01)
*A61B 17/00* (2006.01)

(52) U.S. Cl.
CPC .... *A61B 17/3423* (2013.01); *A61B 17/00234* (2013.01); *A61B 2017/00017* (2013.01); *A61B 2017/00561* (2013.01); *A61B 2017/00893* (2013.01); *A61B 2217/005* (2013.01); *A61B 2217/007* (2013.01)

(58) Field of Classification Search
CPC ............ A61B 17/3421; A61B 17/3423; A61B 17/0218; A61B 17/00234
See application file for complete search history.

(56) References Cited

U.S. PATENT DOCUMENTS 5,183,471 A * 2/1993 Wilk .................... A61B 1/3132 604/284
6,030,365 A 2/2000 Laufer
10,799,266 B2 10/2020 Geisz
2005/0245944 A1* 11/2005 Rezai ................ A61B 17/3421 606/129
2008/0234550 A1 9/2008 Hawkes et al.
2019/0167301 A1* 6/2019 Geisz ................ A61B 17/3421
2019/0200870 A1* 7/2019 Ortega-Quijano ... A61B 5/0084
(Continued)

*Primary Examiner* — Si Ming Ku
(74) *Attorney, Agent, or Firm* — S.J. INTELLECTUAL PROPERTY LTD.

(57) ABSTRACT

The present invention relates to a surgical access port suitable for surgical interventions, characterized by comprising a combination formed by at least one suction conduit and one blowing conduit, such that it allows the surgical field to be cleaned. The inclusion of these cleaning means prevents the surgeon from having to periodically stop the intervention in order to suction and clean the surgical field. The configuration of the access port is such that it allows cleaning, continuously maintaining access to the surgical field and even not requiring the prolongation of elements which descend beyond the port.

15 Claims, 6 Drawing Sheets

(56) References Cited

U.S. PATENT DOCUMENTS

| | | | |
|---|---|---|---|
| 2019/0209154 | A1 | 7/2019 | Richter et al. |
| 2021/0219994 | A1 * | 7/2021 | Muller ............. A61B 17/32002 |
| 2021/0321999 | A1 * | 10/2021 | Walen ................... A61B 90/98 |

* cited by examiner

SURGICAL ACCESS PORT

OBJECT OF THE INVENTION

The present invention relates to a surgical access port suitable for surgical interventions, characterized by comprising a combination formed by at least one suction conduit and one blowing conduit, such that it allows the surgical field to be cleaned.

The inclusion of these cleaning means prevents the surgeon from having to periodically stop the intervention for an assistant intended for this task to have access to the surgical field and to be able to suction and clean the surgical field.

The configuration of the access port is such that it allows cleaning, continuously maintaining access to the surgical field and even not requiring the prolongation of elements which descend beyond the port.

BACKGROUND OF THE INVENTION

In the area of surgery, one of the fields of the art that has been the most intensely developed is the field intended to minimize the damage to tissues caused by a surgical intervention.

One example is the field of minimally invasive surgery, where it is only necessary to open two or three very small windows to insert elements which allow visual access to the inside and also instruments both for sectioning and handling tissues in order to allow interventions which were previously carried out by means of open surgery.

Recovery times with a surgery which so drastically reduces damage to tissues are much shorter and the damages and sequelae produced are also much more minor.

There are operating techniques which require access to the surgical field similar to open surgery, and at the same time, requires minimal damage to tissues in order to access the surgical field. In these cases, access ports which generate a window through which it is possible to access the surgical field are used. This is the case of spine surgeries, where soft tissues are mainly muscle bundles that must remain unsectioned in the direction transverse to the direction of the muscle fiber insofar as possible.

The manner of working and generating these access windows starts with the use of tissue separators. These tissue separators are formed by several elements, among which is a lancet with one end having sectioning capacity. The lancet generates an initial incision at the site where the surgery is to be performed.

The lancet establishes a first section and its presence, given its thickness, generates a first soft tissue dilation. The remaining tissue separating elements are hollow cylindrical bodies such that one houses the next one without leaving any gap or void between them, such that the outer surface of each one is completely fitted snugly against the inner surface of the immediately next one. The cylinder having the smallest diameter has an inner surface adapted for sliding over the surface of the lancet, which is also cylindrical.

With this configuration of the cylindrical elements, after the insertion of the lancet and by keeping it inserted, the next cylinder, which slides over the outer surface of the lancet, is introduced. When the cylinder reaches the soft tissue, it enters said tissue, causing the tissue to even further dilate. The thickness of this cylinder is small so as to avoid causing any tearing or ripping of the patient's soft tissue.

This operation is repeated using the sequence of cylinders having increasingly larger diameters until reaching dimensions that are sufficient for performing the surgery in the surgical field which has been cleared as a result of the sequence of soft tissue separating elements.

A port, which is usually a cylindrical element, having a small thickness, which keeps the surgical field open and allows both the lancet and the set of separating cylinders to be removed from the interior, is inserted as the final element.

This access port is usually fixed either to the table or else to the patient, and it is the port through which the surgeon operates on the patient.

The surgical field therefore is in the deepest area of the window opened through the port. The surgical field is where the surgeon operates, performs sectioning and other operations necessary for surgery.

During these operations, the surgical field becomes fouled by tissue remnants and especially by fluids. The most significant is blood due to the bleeding effect of sectioned tissues, but there may also be blood plasma or irrigation sera introduced in an attempt to clean the area.

The surgical field configuration ends up being a void which may be located at a deeper level than the lower edge of the cylindrical body configuring the port.

Fluids and tissue remnants and other particles, due to the effect of gravity, tend to be stored in the lower area of the void, preventing the surgeon from being able to continue with the operation due to a lack of visibility or effectiveness of the surgeon's tools.

Every time this happens, the surgeon must remove the instruments that are being used by taking them out of the port in order to introduce a suction tube that removes the fluid and solid particles, cleaning the surgical field.

There are times when this is insufficient and cleaning also requires irrigating the area and applying suction again until achieving sufficient cleanliness.

Sectioned tissues usually keep bleeding continuously, and sectioning operations also continuously generate more solid remnants and particles which must be removed. This means that the interruption of the surgical intervention is continuously repeated, slowing down the operation and making the intervention uncomfortable.

Another aspect to be taken into account in this manner of performing surgery is that suction operations are performed manually by handling a suction conduit which requires reaching the lower area of the void where the tissue is located in order to enable the suction to be effective and to remove all the fluid. That is, the end of the suction conduit is handled such that it is introduced until reaching the bottom of the void, and as the operation progresses, said void is located at a level that is increasingly distanced from and below the port. Speaking in terms of level or depth, the end of the suction conduit surpasses the opening of the port in order to be able to reach the bottom of the void; otherwise the fluid could not be suctioned out given that it tends to go to the bottom of said void.

The present invention relates to a surgical access port which allows the surgical field to be cleaned without needing the surgeon to remove instruments, and therefore without stopping the surgical activity, drastically reducing operation time and furthermore keeping the surgical field cleaner.

DESCRIPTION OF THE INVENTION

The invention overcomes the problems previously raised by providing a set of means which establish the cleaning of the surgical field without the need for the surgeon to remove instruments and without the need to introduce conduits which are prolonged beyond the access port to achieve complete cleaning of the void.

According to the invention, the surgical access port, suitable for surgical interventions, comprises:

- a main body configured as a tubular conduit extending according to an axial direction X-X' and comprising:
  - a first access opening arranged at one end of the main body,
  - a second opening arranged at the end of the main body opposite the first opening configured for providing access to a surgical region,
- a suction conduit;
- a blowing conduit configured for providing a gas flow rate in the axial direction and according to a direction of the blowing flow in the operating mode going from the first opening to the second opening.

The main body has a tubular configuration understood in the broadest sense, is formed by a wall not necessarily having a circular section, which is intended for keeping tissues separated and leaving the space therein free. According to certain embodiments, configurations in which the main body does not form a single body, but rather is made up of several elements which form an assembly and expand to dilate soft tissues are considered.

In a preferred way of carrying out the invention, the port has a configuration such that its interior is configured to allow the passage of the separating cylinders which generate the opening in the patient, and in particular of the cylinder having the largest diameter. Nevertheless, it is possible for this port to externally have a configuration other than the cylindrical configuration having a circular section so as to allow additional functions.

This tubular body has a first opening which is the configured for serving as an access for the surgeon and a second opening, arranged at the opposite end of the main body, which provides access to the surgical region. That is, the second opening is located inside the body of the patient and the outer walls adjacent to this opening are in contact with the tissue once the port is inserted in the patient, keeping the opening made in the patient open.

The void in the soft tissue of the patient starts on the surface of the tissue which has initially been perforated for inserting the port and descends through the surface generated while sectioning and the subsequent separation supported by an outer wall segment until reaching the edge of the second opening. The void can be further prolonged beyond the tubular body of the port.

The invention combines two conduits, a first suction conduit and a second blowing conduit configured for generating a flow, preferably of gas, in the axial direction towards the void.

The blowing flow strikes the free surface of the fluid in the void, causing different effects depending on the state of the flow and the remaining conditions.

In a first state of low-speed flow, the air flow strikes the free surface of the fluid, deforming it but without overcoming the surface tension of the fluid. The deformation of the surface of the fluid takes the fluid towards the walls and drives it upwards until reaching the suction conduit which removes all the fluid.

That is, the invention removes all the fluid from the void even though none of the elements of the port and its conduits extends until reaching the bottom of the void, which would imply that they would be in a position interfering with the surgeon's work.

In a subsequent state in which the blowing flow is greater, the surface tension of the fluid is overcome until forming bubbles. Given that the flow is constant, these bubbles are constantly being formed, raising the position of the fluid up to a position higher than in the first state, allowing fluid in the deepest voids to be suctioned out, likewise and surprisingly without the need for any conduit, including the suction conduit, to descend below the second opening, or to even reach the level at which the bottom of the void is located.

According to a third subsequent state in which the blowing flow is greater than that of the second state, the flow forms small, independent fluid bundles which are driven by the air flow out of the access port, reaching the suction conduit even with much greater void depths. That is, the fluid is in the form of droplets which are driven by the main gas flow and transported to where it is suctioned out. The fluid does come out of the first opening given that the suction captures the outflow.

According to an exemplary embodiment of the invention, the main body comprises a perimetral region configured for being supported on biological tissues in the surgical region establishing leak-tightness with said tissues.

According to this exemplary embodiment, the outer surface of the main body has a perimetral region serving as a closure, preventing channels of communication between the void and the exterior outside of the surgical access port from being established. A specific embodiment includes a continuous smooth surface.

According to an exemplary embodiment of the invention, the suction end of the suction conduit is inside the main body.

Although the suction conduit can be either on the inside, for example fitted snugly against the wall, or integrated in the walls of the main body, or even on the outside, its end at which suction takes place is located inside the surgical access port. The blowing action, as described, forces the fluid to move upwards along the side walls, following along the inner wall of the access port until reaching the level at which the end of the suction conduit is located. The fluid is removed at this point.

According to another exemplary embodiment of the invention, the suction end of the suction conduit is outside the main body.

This embodiment of the invention is an alternative to the preceding embodiment, although there are cases in which it is possible to include one or more suction points on the inside and one or more suction points on the outside.

There are times when the void in the patient is generated such that it has a larger diameter than the diameter of the main body having a tubular configuration. In these cases, when the blowing causes the fluid to cling to the walls in order to move upwards along same, given that the void has a larger diameter, the second opening is not in contact with the tissue of the void and moves further in, leaving a perimetral area exposed to the interior of the void. This exposed area establishes a barrier to the fluid which is suctioned when there is a suction point outside the main body.

According to an exemplary embodiment of the invention, the blowing conduit is housed inside the main body.

According to this exemplary embodiment, the blowing generates a gas stream oriented towards the surface of the fluid stored in the void, forcing the fluid, according to any of the states of the flow, to be displaced towards the walls and to move upwards along same as described above.

According to an exemplary embodiment of the invention, the tubular conduit of the main body comprises in the second opening a support annulus configured for establishing support on a rigid tissue.

One of the applications of the invention is bone surgery. One of the preferred examples is spinal column surgery in which, after separating the soft tissues, there is one or more vertebrae at the bottom of the void. According to this embodiment of the invention, the main body has a support annulus intended for being supported on one or more points or regions on the bone or any other rigid tissue.

A specific configuration is one presenting a blunt edge, at least externally, which prevents damaging the rigid tissue under pressure.

According to an exemplary embodiment of the invention, the main body has a conical configuration converging in the axial direction X-X' and towards the second opening.

This configuration has several advantages; the converging configuration causes the second opening of the main body to maintain a small thickness, which allows it to act as another separator in the initial process of insertion into the void with the cylindrical separators still being inserted.

The larger width that is shown in the upper area allows enabling in some embodiments:

- conduits integrated in the walls,
- a first opening having a larger diameter than the second opening to facilitate access from the outside from a larger range of angles, and
- also enabling, for example, an annulus providing functions, such as being a support, and other auxiliary functions, and combining any of the solutions herein listed.

According to an exemplary embodiment of the invention, the blowing conduit is movable according to a radial direction of the tubular conduit of the main body.

According to an exemplary embodiment, the blowing conduit further comprises at least a first position fitting snugly against an internal wall of the main body in the form of a tubular conduit.

The complication existing in the manner of proceeding according to the state of the art in which the surgeon has to periodically move out of the way so as to allow surgical field cleaning operations to be performed by an assistant has been described. According to this embodiment, the blowing conduit allows for a movement in the radial direction such that it can modify the distance to the wall of the surgical access port. This change in position allows changing blowing flow conditions in the void, such that by changing the position of the outlet of the blowing conduit, the conditions of the flow also change, and some particles which do not move under certain flow conditions are caused to move and be removed.

A specific mode allows a first position fitting snugly against the internal wall of the main body, such that it does not hinder the surgeon's work but remains within the port, to be maintained, and the blowing operation can be performed without the surgeon changing position. Since the change in position of the blowing is done by the surgeon, said surgeon can take the instruments to a position which does not impede the change in position of the blowing conduit, such that the blowing operation can be performed under optimal or even changing conditions, and such that the surgeon does not remove any instrument from the surgical access port.

In one exemplary embodiment of the invention, the blowing conduit comprises at least a second position such that its outlet is established in the central position according to the radial direction of the second opening, and also, according to another example, the blowing conduit is movable between the first position and the second position allowing the blowing in any of the intermediate positions in the operating mode.

The blowing conduit thereby not only allows the first position of being fitted snugly against the internal wall of the main body, but also the position of being the farthest away from any of the walls, the central position. Between both positions, the blowing conduit allows any intermediate position, which is very useful in the event of stubborn particles that do not readily come out in the event of a single blowing condition.

According to an exemplary embodiment, the outlet of the gas flow rate of the blowing conduit is mainly in the axial direction and positioned in the center of the section of the main body.

In this specific position, the blowing tends to depress the central area of the fluid due to the higher pressure produced on the fluid-gas interface and causes the fluid to rise along any of the walls with the same probability, which means that the position of the suction point is not altogether relevant.

According to an exemplary embodiment, the end of the blowing conduit is axially spaced from the second opening.

According to this exemplary embodiment, not only is the suction conduit not exposed beyond the second opening, but rather it is also protected against interfering with tissue which may invade the inside of the main body. Nevertheless, it has been experimentally proven that even with the end of the conduit being axially spaced from the second opening, the same effect on the fluid occurs, deforming it or causing the second or third state which raise the fluid up to the suction point.

Also according to an exemplary embodiment, the end of the suction conduit is axially spaced from the second opening.

The fluid raised due to the effect of the flow of the blowing conduit reaches even the suction conduit given that the fluid is first raised along the walls of the void and continues along the inner walls of the surgical access port. This raised position prevents the suction inlet from being blocked by the tissue of the void, and furthermore prevents the presence of elements close to the working region of the surgeon.

The cleaning operation is achieved on the operating region even without any element reaching the bottom of the void, not even with elements coming out of the main body of the access port. It is as if the cleaning was generated remotely, without the intervention of mechanical elements penetrating the surgical field, which always represents a higher risk of infection.

According to an exemplary embodiment, the suction conduit is integrated inside the wall of the tubular conduit formed by the main body.

According to this exemplary embodiment, the suction conduit is not an element occupying part of the space intended for allowing the surgeon to act freely.

According to another exemplary embodiment, the suction conduit (2) comprises a plurality of axially extended channels (2.1) providing a plurality of suction points.

According to this exemplary embodiment, the channels integrated in the main body allow a suction at a plurality of points close to the second opening, maintaining the condition of being integrated in the wall.

According to another exemplary embodiment, it is also possible to include two or more blowing points such that a more complex flow which causes the flow with a given speed to reach different points of the void is allowed to be generated, facilitating the cleaning thereof.

According to an exemplary embodiment, the suction opening is fitted snugly against one side of the wall of the tubular conduit formed by the main body.

According to another exemplary embodiment, the outlet of the blowing conduit is fitted snugly against the wall of the tubular conduit formed by the main body and located diametrically opposite the suction opening.

The position of the suction opening, understood as the end of the suction conduit, fitted snugly against one side of the wall of the tubular conduit formed by the main body allows the suction to be produced at a site where the fluid subjected to the action of the flow generated by the outlet of the gas in the blowing conduit reaches. When the blowing is in the diametrically opposite position, optimal flow conditions are generated given that the recirculation of the flow in the void facilitates the upward movement of the fluid preferably at the site at which the suction is located, achieving greater depth of the void in which the cleaning action is effective.

According to another exemplary embodiment, the suction points of the plurality of suction points are distributed around the perimeter of the tubular conduit formed by the main body.

The suction in which the fluid tends to cling to the wall is facilitated with this configuration. When the plurality of suction ports are equidistantly distributed along the perimeter, it is furthermore possible for the suction to be effective regardless of the conditions in which the operation is being performed and the conditions of symmetry or non-symmetry occurring inside the void.

According to an exemplary embodiment, the surgical access port comprises a distribution ring surrounding the first opening and comprising an inlet port for the suction intake of the vacuum source in fluid communication with the suction point or points.

The possibility of connection allows the easy insertion of the access port into the void of the patient without there being other elements interfering in this operation. The insertion of a suction intake into a vacuum source and the vacuum source acting through a distribution ring allows the suction point to be one in number and located in any position or several in number and for there to be only one inlet connectable to the vacuum source.

A second aspect of the invention relates to a fluid draining system for a surgical region comprising:

- a surgical access port according to any of the preceding claims;
- a vacuum source adapted for providing vacuum conditions in fluid communication with the suction conduit;
- a pressurized gas source adapted for providing pressurized gas in fluid communication with the blowing conduit.

The system has the physical means described and according to any of the configurations already described. Additionally, the system comprises a suction flow rate adjustment device.

This suction flow rate adjustment system allows ensuring that the blown flow does not expel particles out of the access port and that the fluid and particles are suitably removed.

According to an exemplary embodiment, the system further comprises a blowing gas flow rate adjustment device.

The adjustment of the blowing is the most important aspect when establishing the type of flow and state of the fluid in the void to be removed. The flow is established with the adjustment means and in particular according to the following examples.

According to an exemplary embodiment of the invention, the gas flow rate adjustment device is configured for, in the operating mode, providing a gas flow rate such that the Fr number is greater than a first critical value From wherein:

$$Fr = \frac{9800 \cdot H \cdot D^2}{\rho_g v_{ch}^2 d^2}$$

where H is the height between the surgical region and the suction point according to the axial direction X-X', D is the characteristic width of the conduit of the port at its second opening (1.2), $\rho_g$ is the density of the blowing gas used in the operating mode, and $v_{ch}$ is the jet speed at the outlet of the blowing conduit (3) acting in the operating mode, d is the characteristic diameter of the blowing conduit (3), and wherein $Fr_{cr1}$ for establishing the cleaning of a void of at least one height H is less than $Fr_{cr1}$=3.5 for every 10 mm of height H, and more preferably less than $Fr_{cr1}$=3.0 for every 10 mm of height.

Under these conditions, it is ensured that the flow of the fluid is such that it moves according to the first state in which the gas flow modifies the shape of the free surface of the fluid, reducing the level in the area where the gas jet strikes directly and raising the fluid along the walls, first of the void and then, if necessary, on the inside of the cylindrical body of the surgical access port, until reaching the suction point or points.

It has been experimentally proven that the required Fr value is 20% lower when the blowing is located close to the wall, although a blowing preferably located close to the center of the device causes the suction to be possible along any perimetral area, avoiding the problems of jams given that there are always suction alternatives.

Even though the critical Fr number is established for every 10 mm of height to be suctioned, there is a minimum height value of 3 mm which ensure that the tissue of the surgical region does not obstruct the inlet of the suction conduit.

According to another exemplary embodiment, the gas flow rate adjustment device is configured for, in the operating mode, providing a gas flow rate such that the Fr number is less than a second critical value $Fr_{cr2}$, wherein $Fr_{cr2}$=2.5 for every 10 mm of height H to be cleaned, and more preferably is $Fr_{cr2}$=2.0 for every 10 mm of height H to be cleaned, and more preferably is $Fr_{cr2}$=1 for every 10 mm of height H to be cleaned.

By raising the gas outlet speed, the invention switches to the second more effective state and allows the fluid to be raised to a greater height, and it is therefore effective with greater void depths.

According to another exemplary embodiment, the blowing source is a $CO_2$ source.

One of the technical preconceptions when including blowing is the possibility of forcing the entry of gas bubbles into the bloodstream, preferably in situations in which the sectioning of tissues leaves several blood vessels open where the higher pressure may force this entry of gas. It has been found that the use of a $CO_2$ source ensures the flow conditions of the fluid to be removed, and in the event that a bubble is generated in the bloodstream, $CO_2$ is soluble and disappears without causing clots in the patient.

According to an exemplary embodiment, the system comprises an irrigation fluid source adapted for providing pressurized irrigation fluid in communication with an irrigation conduit configured for providing irrigation fluid in the surgical region.

According to another exemplary embodiment, the system further comprises a gas/fluid mixing device with

- a gas inlet port in fluid communication with the pressurized gas source, a fluid inlet port in fluid communication with the irrigation fluid source for the fluid supply, and an outlet port for providing the gas/fluid mixture wherein the outlet port feeds the blowing conduit.

Irrigation of the surgical area allows cleaning to be improved when the removal of fluid is not sufficient. Irrigation provides more fluid in the void of the surgical area, hence the benefit of the combination of blowing and suction, which allows removing the fluid additionally supplied until achieving flushing and cleaning in difficult conditions.

According to another exemplary embodiment, irrigation is performed by using a gas/fluid mixing device such that the outlet is the one used in blowing. According to this configuration, it is possible to incorporate irrigation and blowing through a single conduit, reducing the number of conduits entering the port, and additionally providing a simultaneous supply of irrigation fluid and gas, for example forming a mist necessary for cooling the surgical area.

This irrigation is particularly of interest when the system comprises a robotic arm and when the surgeon acts through the robotic arm with laser scalpels. The laser raises the temperature of the tissue, and once said temperature becomes too high, damages it. The mist allows the temperature to be lowered and in some cases allows the operation with the laser not to be stopped.

According to an exemplary embodiment, the fluid from the irrigation fluid source comprises an excipient and a blood anticoagulant substance.

Irrigation with a fluid incorporating an anticoagulant has been proven to be very effective in preventing excessive blood coagulation, which prevents it from being eliminated, particularly when operating by means of a robot with a sectioning laser.

According to another exemplary embodiment, the gas/fluid mixing device comprises an adjustable dosing device for adjusting the entry of the fluid and is adapted for, in the operating mode:

providing the fluid in the gas stream in the form of droplets; or providing the fluid in the gas stream in the form of mist; and wherein the system comprises a central processing unit adapted for controlling the adjustable dosing device.

This specific exemplary embodiment allows several cleaning modes to be established with varying degrees of aggressiveness with respect to conditions in which cleaning is easy or more difficult, and with more persistent particles. These cleaning modes are programmed in the central processing unit controlling each of the adjustment elements:

According to an operating mode, the central processing unit is at least adapted for controlling the adjustable dosing device such that it establishes the following first operating mode of cleaning the surgical field comprising the following steps:

closing the gas inlet port and opening the fluid inlet port;

closing the fluid inlet port and opening the gas port to remove the fluid from the surgical field.

According to another operating mode, the central processing unit is at least adapted for controlling the adjustable dosing device such that it establishes the following second operating mode of wetting the surgical field comprising the following steps:

opening the gas inlet port and the fluid inlet port and configuring the adjustable dosing device so that the fluid is provided in the gas stream in the form of mist.

According to another operating mode, the central processing unit is at least adapted for controlling the adjustable dosing device such that it establishes the following third operating mode of intensely cleaning the surgical field comprising the following steps:

opening the gas inlet port and the fluid inlet port and configuring the adjustable dosing device so that the fluid is provided in the gas stream in the form of droplets or of a heterogeneous mixture of gas and fluid.

This operating mode has been found to be particularly effective when cleaning the surgical surface, removing even traces of coagulated blood and debris. It has been found that the gas separately and fluid separately do not present the efficacy of this mixture and in these conditions in which the amount of fluid is such that the mixture contains gas and entire fluid bundles which lose their identity as droplets.

It has been observed in these conditions that when the fluid in the void receives the mixture, it also causes bubbling, which helps in this cleaning phase.

According to another operating mode, the central processing unit is at least adapted for controlling the adjustable dosing device such that it establishes the following fourth operating mode of cleaning the surgical field by impact comprising the following steps:

opening the gas inlet port and closing the fluid inlet port to empty the blowing conduit;

opening the fluid inlet port for a first pre-established time period to form a fluid bundle in the blowing conduit and closing the gas inlet port after a second pre-established time period such that the fluid bundle is located in a proximal area of the outlet of the blowing conduit;

opening the gas inlet port to expel and accelerate the fluid bundle against the region of the surgical field;

optionally repeating the last two steps.

The use of the surgical access port by means of a robotic arm performing, for example, sectioning operations by means of laser, has been described above as a very important example. In these cases, the following system examples are established:

A system comprising a surgical intervention laser device configured for, in the operating mode, acting on the surgical field through the tubular conduit of the main body of the surgical access port.

A system wherein the laser device is configured to remain deactivated during the steps of the first operating mode.

This system is configured for cleaning the surgical field without the gas blowing action and with an irrigation phase. It subsequently allows gas blowing and suction to be activated to remove fluid from the surgical field, all with the laser deactivated.

A system wherein the laser device is configured to remain activated during the steps of the second operating mode.

This system is configured for maintaining optimal conditions in robot-assisted operations with a laser. The introduction of a small part of irrigation fluid together with blowing generates a mist which allows wetting the surgical area, preventing the tissues from being burned by the laser action. This mode allows long laser action periods and therefore reduces the surgical operation time.

A system wherein the laser device is configured to remain deactivated during the steps of the third operating mode.

This system is configured for performing a more aggressive or virulent cleaning operation by means of introducing irrigation fluid and gas simultaneously. Under these conditions, the air accelerates the water droplets which act by impacting against the tissues and generating a strongly turbulent flow in the surgical region. This operating mode is suitable when coagulated blood appears in the surgical area and must be removed. This entire operation is performed with the laser preferably deactivated.

A system wherein the laser device is configured to remain deactivated during the steps of the fourth operating mode.

This system is configured for performing an also aggressive cleaning operation but with a different operating mode using fluid bundles that are larger than those that form the droplets. For that purpose, the central processing unit is configured for filling part of the final segment of the blowing tube with irrigation fluid, leaving a fluid bundle in this position. The subsequent sudden entry of pressurized gas expels the fluid bundle at a high speed, impacting against the tissue to be cleaned. According to another example, this mode is performed repeatedly until achieving the target cleanliness. This operating mode is also performed with the laser preferably deactivated.

DESCRIPTION OF THE DRAWINGS

These and other features and advantages of the invention will become more apparent based on the following detailed description of a preferred embodiment given solely by way of illustrative and non-limiting example with reference to the attached figures.

DETAILED DESCRIPTION OF THE INVENTION

According to the first inventive aspect, the present invention relates to a surgical access port suitable for surgical interventions which is useful when the surgical intervention is performed by a surgeon acting manually with surgical instruments that are also manual, and it is also is very useful when the intervention is performed by the surgeon through a robotic arm which can be automated, at least in part, for example, for the application of several sectioning steps according to a given method.

According to an example of interest, the robotic arm uses at least one laser as surgical sectioning instruments.

Throughout both the preceding and the following description, when referring to access by the surgeon to the surgical field, it must be interpreted in a broad sense, where it may refer to a physical person or to a robotic arm unless stated otherwise.

This embodiment shows two types of tissues, a soft tissue (T) in the upper part and a rigid tissue (B), for example bone, in the lower part. The diagram shows a step of the surgical intervention already in progress in which the access port has already been introduced, separating the soft tissues (T), and in which the surgeon has already performed several bone ablation steps generating a void (V).

Figure 1:
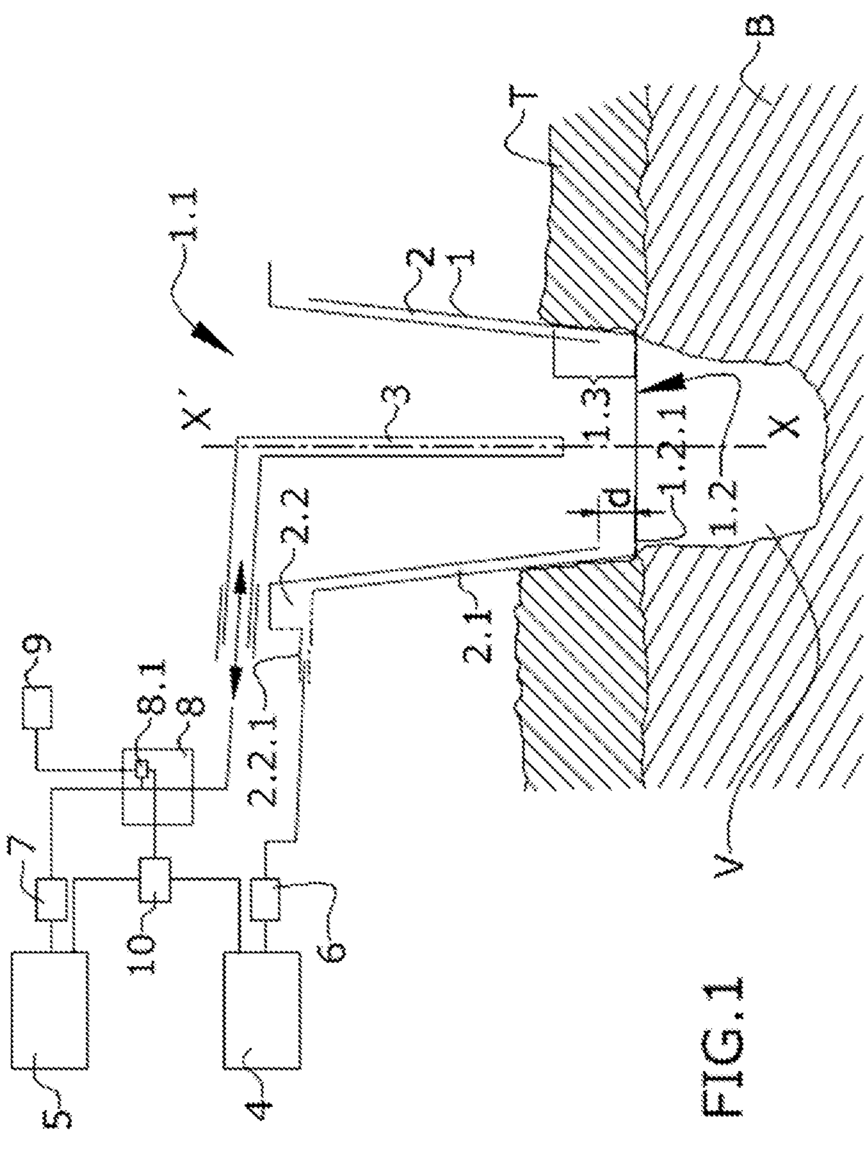
FIG. 1 schematically shows the access port according to a cross-section as well as the additional elements configuring the systems described in various embodiments.

FIG. 1 shows the surgical access port which is shown schematically by means of a main body (1) which has a tubular configuration in this exemplary embodiment. The indication of tubular must be interpreted generically, understanding that the cross-section can be according to a generatrix of a pre-established and closed shape.

FIG. 1 shows a cross-section of the main body (1) in which a first access opening (1.1) is shown in the upper part of the figure and a second opening (1.2) is shown in the lower part.

The first opening (1.1) allows access of the surgeon and has been configured in this embodiment with a larger diameter than the second opening (1.2) which provides direct access to the surgical region.

The surgical access port further comprises a suction conduit (2) which, in this exemplary embodiment shown schematically, is integrated in the walls, leaving the inside of the main body free.

The surgical access port further comprises a blowing conduit (3) configured for providing a gas flow rate in the axial direction X-X'. The axial direction is defined by the main axis of the main body (1) having a tubular configuration.

Figure 2:
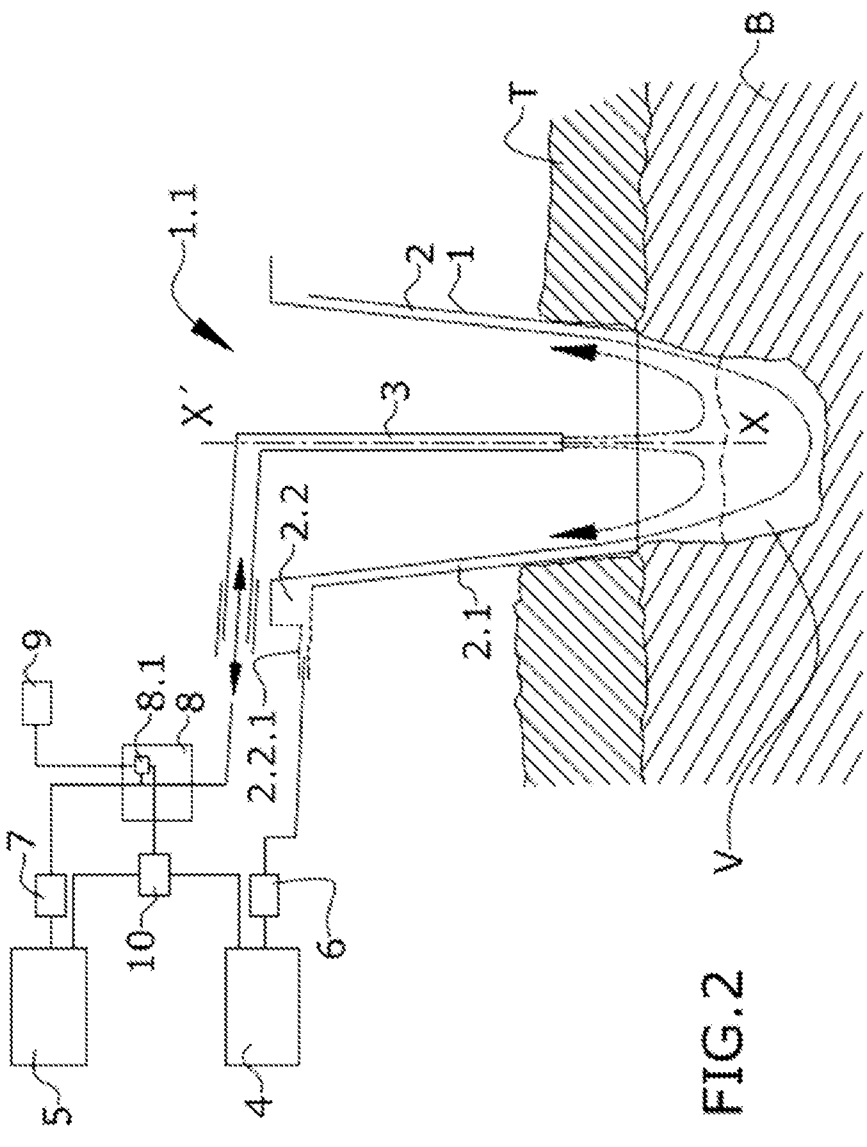
FIG. 2 corresponds to the same example shown in the preceding figure but with visual elements added inside the void in which the surgical region is located for showing the operation in the operating mode. A level of fluid without blowing and the configuration of the free surface when there is blowing are shown by means of different lines.

FIG. 2 shows the void (V) with fluid, with the fluid depicted according to a dashed horizontal line. The continuous line depicts the same fluid when it is subjected to the blowing action.

Both in FIG. 1 and in FIG. 2, an outer perimetral region (1.3) of the main body (1.3) is a surface part intended for keeping the soft tissues (T) separated. In this exemplary embodiment, the lower part of the main body (1) also has a support annulus (1.2.1) which allows for better support on the rigid tissue (B) without damaging it.

In these exemplary embodiments, the outlet of the blowing conduit (3) is aimed in the axial direction X-X' towards the void (V), giving rise to a gas flow which descends through the central part, strikes the fluid increasing the pressure and generates a boundary layer in the radial direction both in the gas and in the fluid which generates a driving force driving the fluid towards the wall. This same force generates the upward movement of the fluid along the walls until reaching the opening of the suction conduit (2), where said fluid is removed until it all disappears from the void (V).

In this exemplary embodiment, the inlet opening of the suction conduit (2) is also spaced a distance d from the second opening (1.1) such that the soft tissue does not block its inlet.

In this exemplary embodiment, the suction conduit (2) is formed by a plurality of channels (2.1) integrated in the wall of the main body (1) which move upwards until meeting with a vacuum distribution ring (2.2) located in the upper part.

In this same diagram shown in FIGS. 1 and 2, in the upper part of the main body (1), the blowing conduit (3) shows by means of two-way arrows the possible displacement of the blowing conduit (3) in which said blowing conduit (3) can be displaced according to the radial direction, that is, the direction perpendicular to the axial direction X-X', for being moved between at least two end positions, an end position fitting snugly against the wall of the main body, not shown in the figures, and another end position located in the center, such as the position shown in FIGS. 1 and 2.

The position fitting snugly against the internal wall of the main body (1) leaves the inside of the access port free. The possibility of the blowing conduit (3) being able to be located in any intermediate position between the two end positions allows more effective cleaning operations when there are coagula or stubborn particles that do not readily become detached.

Both FIG. 1 and FIG. 2 show a vacuum source (4) after which there is located a suction flow rate adjustment device (6). Throughout the entire description the term vacuum source is used, understanding it to be a source having a pressure less than atmospheric pressure and not necessarily in absolute vacuum conditions. That is, by controlling the change from a closed position to an open or half-open position in the suction flow rate adjustment device (6), a controlled suction is established at the end of the suction conduit (2).

The same occurs with the gas flow rate adjustment device (7); when said device receives a command to open, the pressure of the gas source (5) greater than atmospheric pressure allows a blowing flow, which is adjusted depending on how much said gas flow rate adjustment device (7) is opened, to be established.

Both flow rate adjustment devices (6, 7) are controlled by a central processing unit (10) which can be one in number or distributed.

According to another exemplary embodiment, the system comprises a gas/fluid mixing system (8) comprising at least two inlets, one through a gas inlet port in fluid communication with the pressurized gas source (5), for example, through the gas flow rate adjustment device (7), and a second inlet through a fluid inlet port in fluid communication with an irrigation fluid source (9) intended for supplying irrigation fluid.

The mixing of the gas and of the irrigation fluid inside the gas/fluid mixing device (8) is established by means of an adjustable dosing device (8.1) also in communication with the central processing unit (10).

Figure 3A:
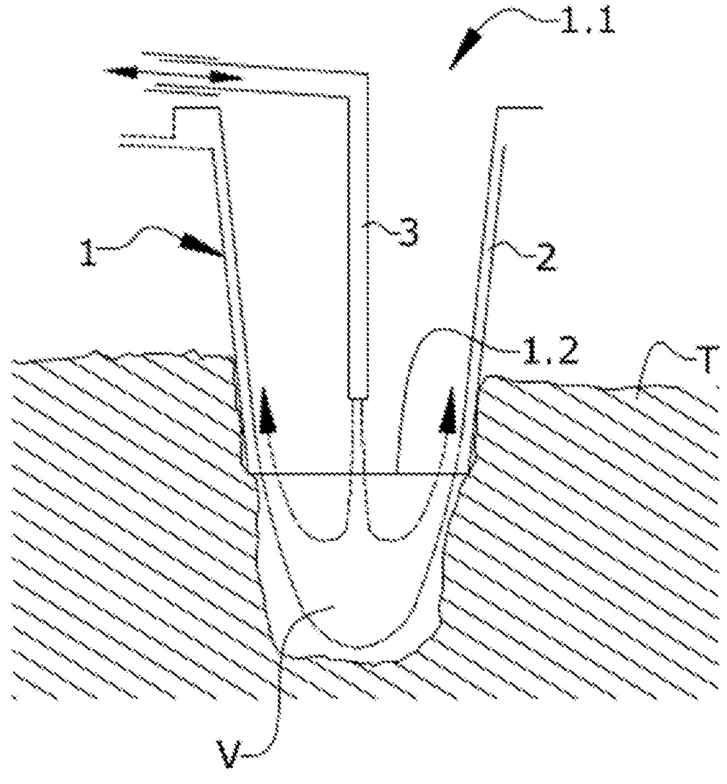
FIG. 3A schematically shows the combined action of blowing and suction in a void according to an exemplary embodiment in which the soft tissue is completely fitted snugly against the access port.

FIG. 3A shows a diagram in which the tissue (T) separated by the surgical access port is in contact with the main body (1) right up to the second opening (1.2). Therefore, when the blowing through the blowing conduit (3) is activated, the gas flow impacts against the free surface of the fluid, causing the fluid to be displaced to the side walls along which it moves upwards. Given the continuity between the wall of the void (V) and the internal wall of the main body (1), the fluid continues moving upwards along the internal wall of the main body (1) when it reaches the access port until reaching the inlet of the suction conduit (2).

Figure 3B:
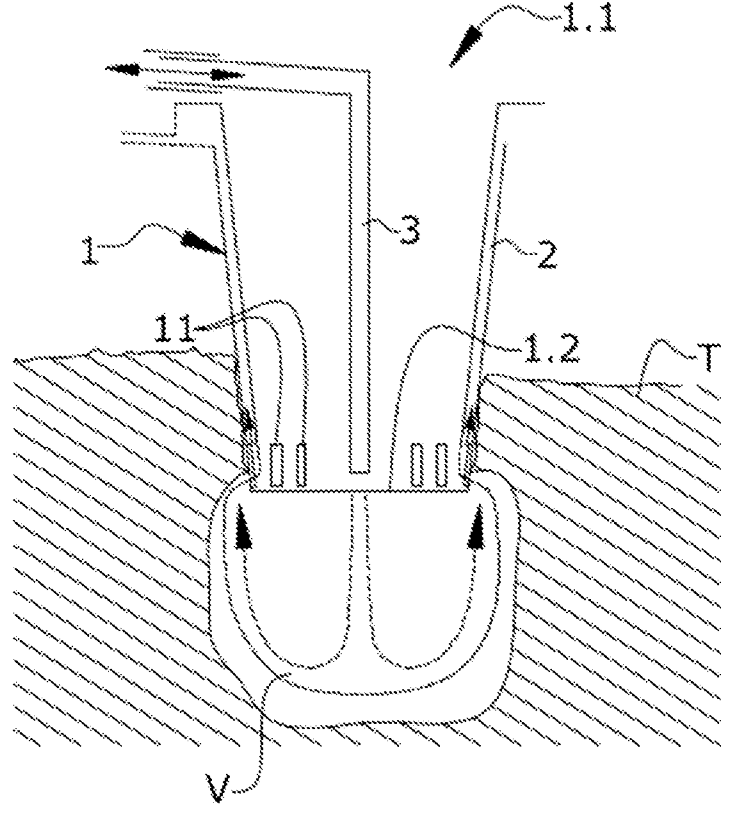
FIG. 3B shows a situation in which the void in the tissue is larger and is not completely fitted snugly against the outer wall of the access port. In this case, an exemplary embodiment adapted for effectively operating even under these circumstances is shown.

FIG. 3B shows a diagram in which the tissue (T) separated by the surgical access port is in contact with the main body (1) in a perimetral segment but is not in contact in a region close to the opening (1.2). In the case of the same blowing conditions as those shown in FIG. 3A, the fluid moves upwards along the walls of the void (T) until meeting with the access port. Given that now there is no continuity between the internal wall of the void (T) and the internal wall of the main body (1), the fluid meets with the external wall of the main body (1) which acts as a barrier preventing its access into the main body in which the inlet to the suction conduit (2) is located. That is, under these circumstances, the suction is not effective and the desired effect is not produced.

According to an exemplary embodiment of the invention, this problem is overcome by incorporating windows (11) in the lower part of the main body, proximal to the second opening (1.2), communicating the outer and inner parts of the main body. The fluid moving upwards due to the blowing effect can thereby go from the outer wall to the inner wall and subsequently be suctioned out.

Figures 4A, 4B:
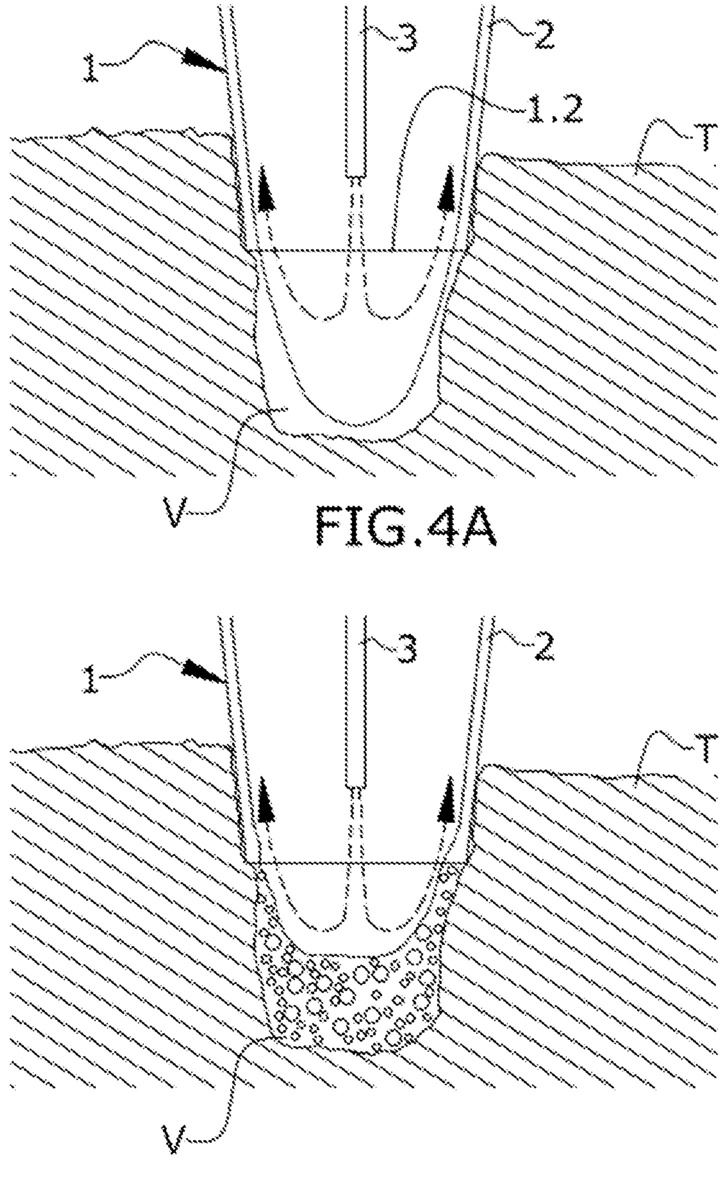
FIGS. 4A-4C show a sequence corresponding to a first state, a second state, and a third state with increasingly higher gas speeds, such that the fluid removal mechanism is different and allows the removal thereof from increasingly deeper voids.
Figure 4C:
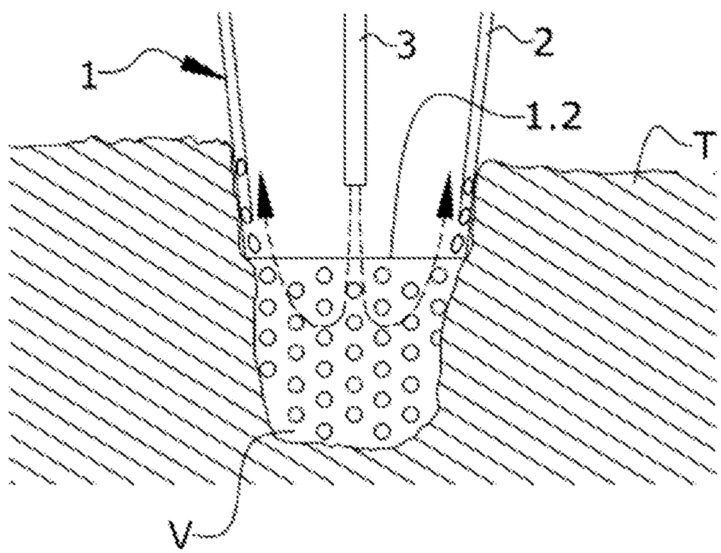

The sequence of FIGS. 4A, 4B, and 4C show the three possible states of flow. FIG. 4A shows a first state of flow in which the outlet speed is such that the Fr number is greater than a first critical value $Fr_{cr1}$ of 0.5 wherein:

$$Fr = \frac{9800 \cdot H \cdot D^2}{\rho_g v_{ch}^2 d^2}$$

where H is the height between the surgical region and the suction point according to the axial direction X-X', D is the characteristic width of the conduit of the port at its second opening (1.2), $\rho_g$ is the density of the blowing gas used in the operating mode, and $v_{ch}$ is the jet speed at the outlet of the blowing conduit (3) acting in the operating mode, d is the characteristic diameter of the blowing conduit (3).

The upward movement effect through the walls until reaching the opening of the suction conduit (2), removing the fluid, is ensured under these conditions.

FIG. 4B shows a second state of the gas in which the outlet speed of the gas jet is such that it breaks the surface of the fluid, generating bubbles inside said fluid. The specific weight of the fluid is thereby reduced, and also the higher surface driving effort allows the fluid to be raised to greater heights.

FIG. 4C shows a third state of air/fluid flow in which now the gas impacts at a higher speed against the fluid, constantly overcoming the surface tension of the fluid such that there are formed fluid bundles or droplets which are driven by the gas flow until reaching the opening of the suction conduit (2), even though it is at a very high height.

These three types of state are applicable to any of the described exemplary embodiments and are determined by the flow rate adjustment device (7) and controlled by the central processing unit (10).

Any of the described exemplary embodiments also allow both the blowing and the suction flow rate adjustment devices to be adjusted manually and not necessarily through the central processing unit (10).

The invention claimed is:

1. A fluid draining system for a surgical region comprising:

- a surgical access port suitable for surgical interventions, comprising:
  - a main body configured as a tubular conduit extending according to an axial direction X-X' and comprising:
    - a first access opening arranged at one end of the main body;
    - a second opening arranged at the end of the main body opposite the first opening configured for providing access to a surgical region;
    - a suction conduit;
    - a blowing conduit configured for providing a gas flow rate in the axial direction and according to a direction of the blowing flow in an operating mode going from the first opening to the second opening;

a vacuum source adapted for providing vacuum conditions in fluid communication with the suction conduit;

a pressurized gas source adapted for providing pressurized gas in fluid communication with the blowing conduit;

a blowing gas flow rate adjustment device; and wherein the blowing gas flow rate adjustment device is configured for, in the operating mode, providing a gas flow rate such that the Er number is greater than a first critical value $Fr_{cr1}$ wherein:

$$Fr = \frac{9800 \cdot H \cdot D^2}{\rho_g v_{ch}^2 d^2}$$

where H is the height between the surgical region and a suction point according to the axial direction X-X", D is a characteristic width of the conduit of the port at its second opening, $\rho_s$ is a density of the blowing gas used in the operating mode, and $v_{ch}$ is a jet speed at the outlet of the blowing conduit acting in the operating mode, d is a characteristic diameter of the blowing conduit, and wherein $Fr_{cr1}$ for establishing cleaning of a void of at least one height H is less than $Fr_{cr1}$=3.0 for every 10 mm of height H.

2. The system according to claim 1, comprising a suction flow rate adjustment device.

3. The system according to claim 1, wherein a blowing gas flow rate adjustment device is configured for, in the operating mode, providing a gas flow rate such that the Fr number is less than a second critical value $Fr_{cr2}$, wherein $Fr_{cr2}$ in the range of 1 to 2.5 for every 10 mm of height H to be cleaned.

4. The system according to claim 3, further comprising an irrigation fluid source adapted for providing pressurized irrigation fluid in communication with an irrigation conduit configured for providing irrigation fluid in the surgical region.

5. The system according to claim 4, further comprising a gas/fluid mixing device with a gas inlet port in fluid communication with the pressurized gas source, a fluid inlet port in fluid communication with the irrigation fluid source for a fluid supply, and an outlet port for providing the gas/fluid mixture, wherein the outlet port feeds the blowing conduit.

6. The system according to claim 5, wherein the gas/fluid mixing device comprises an adjustable dosing device for adjusting an entry of the fluid and is adapted for, in the operating mode:

providing the fluid in the gas stream in the form of droplets; or providing the fluid in the gas stream in the form of mist; and wherein the system comprises a central processing unit adapted for controlling the adjustable dosing device.

7. The system according to claim 6, wherein the central processing unit is at least adapted for controlling the adjustable dosing device such that it is configured to at least establish one of the four following operating modes:

the first operating mode of cleaning a surgical field by carrying out the following steps:

closing the gas inlet port and opening the fluid inlet port; and closing the fluid inlet port and opening the gas port to remove the fluid from the surgical field;

the second operating mode of wetting the surgical field by carrying out the following steps: opening the gas inlet port and the fluid inlet port and configuring the adjustable dosing device so that the fluid is provided in the gas stream in the form of mist;

the third operating mode of intensely cleaning the surgical field by carrying out the following steps: opening the gas inlet port and the fluid inlet port and configuring the adjustable dosing device so that the fluid is provided in the gas stream in the form of droplets;

the fourth operating mode of cleaning the surgical field by impact by carrying out the following steps or any combination thereof:

opening the gas inlet port and closing the fluid inlet port to empty the blowing conduit:

opening the fluid inlet port for a first pre-established time period to form a fluid bundle in the blowing conduit and closing the gas inlet port after a second pre-established time period such that the fluid bundle is located in a proximal area of the outlet of the blowing conduit;

opening the gas inlet port to expel and accelerate the fluid bundle against the region of the surgical field; and optionally repeating the last two steps.

8. The system according to claim 7, comprising a surgical intervention laser device configured for, in the operating mode, acting on the surgical field through the tubular conduit of the main body of the surgical access port.

9. The system according to claim 7, comprising a surgical intervention laser device configured for, in the operating mode, acting on the surgical field through the tubular conduit of the main body of the surgical access port, wherein the laser device is configured to remain deactivated during the steps of the first operating mode.

10. The system according to claim 1, wherein the blowing conduit of the surgical access port is movable according to a radial direction of the tubular conduit of the main body.

11. The system according to claim 1, wherein the blowing conduit comprises:

at least a first position fitting leaning against an internal wall of the tubular conduit; and/or at least a second position such that its outlet is established in a central position according to a radial direction of the second opening;

wherein the blowing conduit is movable between the first position and the second position allowing the blowing in any of a plurality of intermediate positions in the operating mode.

12. The system according to claim 1, wherein the suction conduit is integrated inside a wall of the tubular conduit formed by the main body.

13. The system according to claim 1, wherein the suction conduit comprises a plurality of axially extended channels providing a plurality of suction points.

14. The system according to claim 13, wherein suction points of the plurality of suction points are distributed around a perimeter of the tubular conduit formed by the main body.

15. The system according to claim 13, wherein the surgical access port comprises a distribution ring surrounding the first opening and comprising an inlet port for a suction intake of the vacuum source in fluid communication with the suction points.

* * * * *